United States Patent [19]

Funk, Jr. et al.

[11] 3,954,867

[45] May 4, 1976

[54] CONTINUOUS PROCESS FOR PREPARING METHYLENE DIANILINES

[76] Inventors: Bernard D. Funk, Jr., 627 Regal St., Houston, Tex. 77034; Jerardo Mongiello, 102 Lazy Lane, Baytown, Tex. 78340; Warren J. Rabourn, 1202 E. Princeton Lane, Deer Park, Tex. 77536

[22] Filed: June 11, 1973

[21] Appl. No.: 368,876

Related U.S. Application Data

[63] Continuation of Ser. No. 867,690, Oct. 20, 1969, abandoned.

[52] U.S. Cl. ................. 260/570 D; 260/453 AM
[51] Int. Cl. ............................................. C07c 85/08
[58] Field of Search .............................. 260/570 D

[56] References Cited
UNITED STATES PATENTS

| | | | |
|---|---|---|---|
| 3,260,751 | 7/1966 | Powers et al. | 260/570 |
| 3,277,139 | 10/1966 | Powers | 260/570 |
| 3,478,099 | 11/1969 | Ross et al. | 260/570 |
| 3,496,229 | 2/1970 | Powers et al. | 260/570 |
| 3,517,062 | 6/1970 | Powers | 260/570 |

*Primary Examiner*—R. V. Hines

[57] ABSTRACT

A continuous process is described for the preparation of methylene-bridged polyphenyl polyamines containing di(aminophenyl)methane having a high, p,p'-isomer content (at least 98 percent by weight). Fluid streams of aqueous aniline hydrochloride solution and aqueous formaldehyde are intermixed at one end of a continuous tubular reactor, passed therethrough at 0°C to 75°C in about 3 seconds to about 120 seconds, thence to recycle in a cooling zone (less than 60°C), optionally to a holding zone (temperature less than 70°C) and finally to a final reaction zone (temperature 60°C to 120°C) to complete the reaction. The diamine content in the polyamines is controlled by molar ratio of aniline hydrochloride to formaldehyde in the feeds. Preferably the holding zone, where employed, and final reaction zone comprise a continuous tubular vessel.

12 Claims, 3 Drawing Figures

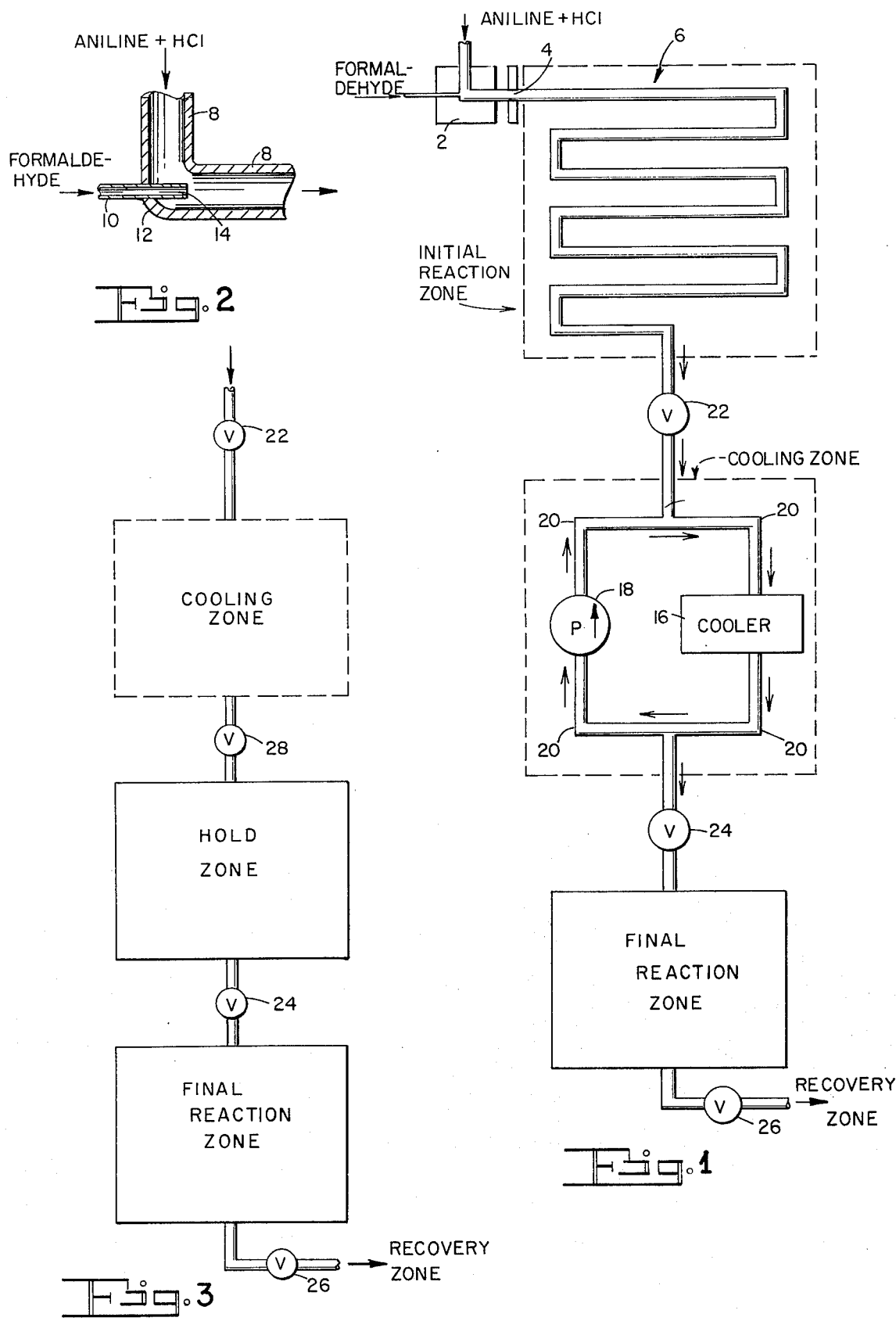

CONTINUOUS PROCESS FOR PREPARING METHYLENE DIANILINES

This application is a continuation of our copending application Ser. No. 867,690 filed Oct. 20, 1969 and now abandoned.

BACKGROUND OF THE INVENTION

1. Field of the Invention

This invention relates to the preparation of polyamines and is more particularly concerned with the continuous preparation of methylene-bridged polyphenyl polyamines by acid condensation of aniline and formaldehyde.

2. Description of the Prior Art

The acid condensation of aniline and formaldehyde to produce a mixture of methylene-bridged polyphenyl polyamines containing a major portion of di(aminophenyl)methane is well-recognized in the art; see, for example, U.S. Pat. Nos. 2,938,054; 3,163,666; 3,260,751; 3,274,247; and 3,277,173. The mixture of polyamines can be used for a variety of purposes, for example, as a source of pure di(4-aminophenyl)methane (MDA) which is useful as an epoxy resin curative and an intermediate in the preparation of di(4-aminocyclohexyl)methane ($H_{12}$MDA). Both the MDA and $H_{12}$MDA are useful in the preparation of polyamides; see, for example, U.S. Pat. Nos. 2,669,556 and 3,416,302, respectively.

Alterntively, the mixture of polyamines can be phosgenated, by procedures well-known in the art, to the corresponding mixture of polymethylene polyphenyl polyisocyanates containing methylenebix(phenyl isocyanate) as the major component. The latter can be recovered from said mixture, if desired, and finds broad application in the preparation of elastomeric and other non-cellular polyurethanes. In addition, the mixture of polymethylene polyphenyl polyisocyanates obtained in the above phosgenation is widely used in industry in the manufacture of cellular polyurethanes. Recently there has been described a highly useful process of recovering methylenebis(phenyl ioscyanate) and a mixture of polymethylene polyphenyl polyisocyanates continuously and simultaneously from a polymethylene polyphenyl polyisocyanates feedstock containing a high proportion (65 to 75 percent by weight) of methylenebis(phenyl isocyanates); see, British Patent No. 1,092,019.

For many of the purposes for which the di(aminophenyl)methane and methylenebis(phenyl isocyanates), obtained as described above, are to be used, it is desirable that these materials be prepared in the form of the substantially pure 4,4'-isomer (i.e. at least 98 percent by weight). The presence of significant amounts of the corresponding 2,4'- and 2,2'-isomers in these materials is undesirable particularly where the materials are to be used in the preparation of polyamide and polyurethane fibers and filaments.

Hitherto it has been necessary to submit the diamine or diisocyanate obtained as described above to purification procedures such as fractional distillation, fractional crystallization, and the like, in order to obtain the desired 4,4'-isomers free from significant amounts of the corresponding 2,4'- and 2,2'-isomers. Such purification methods are cumbersome on the manufacturing scale and add significantly to the cost of producing the end-product.

We have now found that it is possible, by means of the novel process described hereinafter, to produce directly, in a continuous manner, a mixture of polyamines in which the di(aminophenyl)methane component is present in the form of the substantially pure 4,4'-isomer (purity of at least 98 percent by weight) and thereby to avoid the necessity to embark upon extensive purification of this diamine, or of the corresponding diisocyanate to which it is converted by phosgenation. This finding is of considerable commercial importance and enables the production of the aforementioned diamine and diisocyanate to be accomplished at considerable savings in cost.

Further, the process of the present invention can be used to prepare methylene-bridged polyphenyl polyamines which are phosgenated to produce the feedstock for the process described in the aforesaid British Patent No. 1,092,019. It is possible thereby to follow a remarkably economic route to the simmultaneous production of substantially pure 4,4'-methylenebis(phenyl ioscyanate) and polymethylene polyphenyl polyisocyanates.

These various advantages in the process of the present invention mark a clear advance over previously described continuous processes for the production of methylene-bridged polyphenyl polyamines.

SUMMARY OF THE INVENTION

The invention, in its broadest aspect, comprises a continuous process for the preparation of methylene-bridged polyphenyl polyamines containing di(aminophenyl)methane having a high p,p'-isomer content, which process comprises the steps of:

intermixing, at a temperature of about 0°C to about 60°C, rapidly flowing fluid streams of aqueous aniline hydrochloride and aqueous formaldehyde, in the proportion of from about 4.0 moles to 1.5 moles of aniline per mole formaldehyde, at the entry port of a continuous tubular reactor;

causing said intermixed fluid streams to flow through said tubular reactor at such a rate that substantially no backmixing occurs while maintaining the temperature of the reaction mixture in said tubular reactor below about 75°C;

continuously passing said reaction mixture from the exit port of said tubular reactor to a cooling zone in which said reaction mixture is continuously recycled so as to maintain the temperature of said reaction mixture below about 60°C but above the temperture at which solid material separates from the mixture;

continuously removing reaction mixture from said cooling zone at a rate corresponding to that at which reaction mixture is fed to said cooling zone from said tubular reactor;

continuously passing reaction mixture removed from said cooling zone to a final reaction zone in which the temperature of the reaction mixture is maintained within the range of about 60°C to about 120°C; and continuously removing from said final reaction zone a mixture of methylene-bridged polyphenyl polyamines at a rate corresponding to that at which the intermediate reaction mixture from said cooling zone is passed to the final reaction zone.

BRIEF DESCRIPTION OF THE DRAWINGS

FIG. 1 shows a flow sheet illustrating the steps in a specific embodiment of a process according to the invention.

FIG. 2 shows a cross-sectional view of a particular embodiment of a mixing apparatus employed in the process of the invention.

FIG. 3 shows a flow sheet illustrating the steps in a second specific embodiment of a process according to the invention.

DETAILED DESCRIPTION OF THE INVENTION

The process of the invention comprises a novel combination of steps which combination permits the production of methylene-bridged polyphenyl polyamines on a continuous basis. Further the process is readily adapted to the production of methylene-bridged polyphenyl polyamines having a wide range of content of di(aminophenyl)methane. More particularly the di(aminophenyl)methane present in the reaction product is substantially pure 4,4'-isomer, i.e. contains at least 98 percent by weight of that isomer. This combination of advantages in the process of the invention is brought about, in part, by careful control of the reaction conditions at the various stages and, in part, by the novel design and mode of operation of said various stages.

In the initial step of the process of the invention, the aniline, hydrochloric acid, and formaldehyde are brought together and mixed in appropriate proportions in the form of aqueous solutions. The aniline and hydrochloric acid are premixed and then treated as a single stream to be mixed with the aqueous formaldehyde solution.

In general, the amount of hydrochloric acid employed is less than that required to completely neutralize the aniline. The proportion of hydrochloric acid employed is advantageously within the range of about 0.95 equivalent to about 0.45 equivalent per equivalent of aniline. The amount of hydrochloric acid employed in any particular case depends upon the proportion of di(aminophenyl)methane desired in the end product. The other factors which control the proportion of diamine are discussed hereinafter. The higher concentrations of hydrochloric acid in the above-stated range are employed when the higher concentration of diamine in the end product is desired. Conversely the lower concentration of hydrochloric acid in the above range are employed when the lower concentration of diamine in the end product is desired.

As will be seen from the above proportions, the aqueous solution of aniline and hydrochloric acid employed in the initial step of the process of the invention is a mixture of aniline hydrochloride and free aniline. The overall concentration of aniline and aniline hydrochloride in the solution employed in this step is important. Advantageously, the concentration is such that the molar proportion of water to aniline (as free base and hydrochloride) in said feed stream is of the order of about 1.3:1 to about 7.6:1, and preferably said molar proportion is of the order of about 2.1:1 to about 3.8:1.

Similarly, the concentration of formaldehyde, in the aqueous solution thereof which forms the second feed stream, is important and is advantageously such that the molar proportion of water to formaldehyde is within the range of about 2.0:1 to about 15.0:1, and preferably said molar ratio is within the range of about 2.8:1 to about 8.4:1.

The optimum total water in the mixed feed stream is important. The total water ranges advantageously from 4 to 7 moles per mole of aniline or from 7 to 15 moles of water per mole of formaldehyde.

The two feed streams are brought together at relatively high rates of flow under conditions which ensure highly efficient mixing of the streams. Reference is made to FIG. 1 wherein there is shown a schematic flow sheet of a process according to the invention. The aniline-hydrochloric acid stream and the formaldehyde stream are shown therein as being brought together in the mixer 2 which is disposed so that the mixed feed flowing therefrom passes directly to the entry port 4 of a tubulr reactor 6. As the mixer 2 there can be used any of a wide variety of apparatus commonly used in the art for the mixing of moving liquid streams. For example, the mixer 2 can take the form of a standard impeller type pump which is adapted so that the formaldehyde stream is conducted to the center of the impeller and there injected into the aniline-hydrochloric acid stream which is flowing through the pump. In a further illustration of the apparatus which can be employed as the mixer 2 there can be used a thin film reactor mix nozzle of the type shown in U.S. Pat. No. 3,154,103 for the mixing of gaseous fluids. Included in the types of mixing apparatus which can be employed as the mixer 2 are the various T-junction devices commonly employed in the mixing of fluid streams.

A particularly useful mixing apparatus which can be enployed with advantage as the mixer 2 is that which is shown in cross-section in FIG. 2. In the embodiment shown in FIG. 2, the aniline-hydrochloric acid stream is fed through angle tube 8 from which it flows directly into the entry port 4 of the tubular reactor 6 of FIG. 1. The formaldehyde stream is introduced directly into the aniline-hydrochloride stream via the injector tube 10 which is mounted in said angle tube 8 immediately above the angle 12 thereof. The tube 10 is shown in FIG. 2 as mounted so that its axis is substantially concentric with that of the lower portion of angle tube 8 which leads directly to the tubular reactor 6. However said tube 10 can, if desired, be mounted so that its axis is parallel to, but not necessarily concentric with, that of said lower portion of angle tube 8.

In the particular embodiment of FIG. 2, the exit port 14 of injector tube 10 is shown as projecting into the angle tube 8 a distance such that it is clear of the bend in said angle tube 8. However, the location of exit port 14 can be varied all the way from a position which is substantially flush with the side wall of angle tube 8 through which the injector tube 10 passes, up to and including a position in which the exit port 14 is situated a substantial distance within the lower half of angle tube 8 beyond the particular position shown in FIG. 2. The most favorable position for exit port 14 for any given set of processing conditions can be determined by a process of trial and error. In a further variation of the mixing apparatus shown in FIG. 2, there can be employed a plurality of injector tubes 10 in place of the single tube 10 shown in FIG. 2.

Referring again to the flow sheet shown in FIG. 1, the relative porportions in which the aniline-hydrochloric acid stream and the formaldehyde stream are mixed in mixer 2 is determined largely by the required composition of the mixture of methylene-bridged polyphenyl polyamines which is to be prepared. Illustratively, the use of a molar ratio of aniline to formaldehyde of about 1.6:1.0 will give rise to a mixture of methylene-bridged polyphenyl polyamines containing approximately 40 percent by weight of di(aminophenyl)methane; see U.S. Pat. No. 2,683,730. On the other hand, the use of a molar ratio of aniline to formaldehyde of about 4:1 will give rise to a mixture of methylene-bridged polyphenyl polyamines containing approximately 85 percent by weight of di(aminophenyl)methane; see U.S. Pat. No. 2,950,263. The use of aniline to formaldehyde ratios in the range between the above two extremes yields methylene-bridged polyphenyl polyamine mixtures having a content of di(aminophenyl)methane intermediate between the extreme levels set forth above. The precise ratio of aniline to formaldehyde required to produce any desired level of di(aminophenyl)methane in the methylene-bridged polyphenyl polyamine mixture can be determined by a process of trial and error.

The aniline-hydrochloric acid and formaldehyde stream, fed to the mixer 2, in the required proportions determined as described above, are preferably each at a temperature below about 50°C, but consistent with maintenance of fluidity, prior to the mixing step. The most preferred temperature at which these streams are brought together for mixing is of the order of about 20°C to about 45°C. The rates at which the two feed streams are introduced into the mixer 2 will vary according to a number of factors including the capacity of the mixer 2 and of the tubular reactor 4 and the desired throughput. Said rates will obviously influence the efficiency of mixing in the mixer 2 and in the reaction mixture as it passes through the tubular reactor 6. In general, the rates of flow of feed streams are adjusted, by a process of trial and error, for any given device 2 so as to avoid substantially any back-mixing in the reaction mixture during its passage into and through the tubular reactor 6. Back-mixing is a term employed conventionally in the art to mean the intermixing of material at a more advanced stage of processing with material at a less advanced stage of processing.

Said tubular reactor 6 is represented as having a coiled configuration in the embodiment shown in FIG. 1. It is to be understood that the configuration of reactor 6 is immaterial to the operation of the process of the invention and any configuration, including a straight line configuration, can be employed. Said tubular reactor 6 is advantageously provided with a cooling jacket (not shown). The temperature of the reaction mixture as it passes through said reactor 6 is thereby controlled so that advantageously it is within the range of about 0°C to about 75°C, and preferably within the range of about 20°C to about 50°C. The rate of flow of reaction mixture and the overall dimensions of the reactor 6 are adjusted so that the average residence time of reaction mixture in said reactor 6 is not more than about 120 seconds. Preferably the average residence time of reaction mixture in said reactor 6 is less than about 20 seconds. The use of residence time of this low order of magnitude is critical in terms of attainment of the overall desired result in the process of the invention.

The reaction between formaldehyde and aniline is highly exothermic. The above residence times within the tubular reactor 6 ensure that the reaction mixture has passed through said reactor 6 prior to the onset of the major exothermic phase of the reaction and is in the next zone, i.e. the COOLING ZONE shown in FIG. 1, before the latter phase is encountered.

The COOLING ZONE shown schematically in FIG. 1 comprises a loop 20 having a cooler 16 through which the reaction mixture is continuously recycled utilizing a pump 18. The cooler 16 can be any standard form of unit having the necessary capacity to maintain the temperature of the reaction mixture below about 60°C and preferably below about 50°C. The lower level of temperature at which the reaction mixture can be maintained in the COOLING ZONE is dictated by the properties of the reaction mixture. Thus the preferred lower temperature of operation is the lowest temperature at which the reaction mixture can be held without separation of solids. As stated above, the reaction mixture is in the stage of maximum exotherm during its residency in the COOLING ZONE and, accordingly, the capacity of the cooler 16 is required to be substantial.

By appropriate adjustment of valve 24, which controls the rate at which reaction mixture leaves the COOLING ZONE, it is possible to remove reaction mixture continuously from the COOLING ZONE, for transfer to the FINAL REACTION ZONE at the same rate as reaction mixture enters the COOLING ZONE from the tubular reactor 6, thereby maintaining a steady state in said COOLING ZONE. Similarly, by appropriate adjustment of rates of flow using said valve 24 and adjustment of the capacity of the COOLING ZONE, it is possible to vary the average residence time of reaction mixture in said COOLING ZONE to any desired extent. Advantageously, the average residence time of reaction mixture within said COOLING ZONE is within the range of about 4 minutes to about 50 minutes. Preferably said average residence time is of the order of about 10 minutes to about 30 minutes, the final selection depending largely upon the temperature at which the reaction mixture is maintained during its residence, i.e. in general, the lower the temperature is the COOLING ZONE, the longer the permissible average residence time.

The reaction mixture which is continuously withdrawn from the COOLING ZONE in the above manner is then passed to a FINAL REACTION ZONE. In the latter the reaction mixture is heated to a temperature within the range of about 60°C to about 120°C, preferably within the range of about 80°C to about 100°C. The period of time for which the heating is carried out is generally at least sufficient to ensure completion of formation of methylene-bridged polyphenyl polyamines. As will be apparent to one skilled in the art, the higher the reaction temperature employed in the FINAL REACTION ZONE, the shorter the period required for completion of reaction. The time required for completion of any given temperature can be determined readily by trial and error.

The FINAL REACTION ZONE can take the form of any suitable reaction vessel which is equipped with appropriate means for controlling reaction temperature etc. and, preferably, is of such a design that back-mixing is minimized. In a preferred embodiment, the FINAL REACTION ZONE takes the form of a continuous tube of appropriate diameter and length to provide the necessary hold-up or residence time of the reaction mixture. Said tube is heated by appropriate jacketing and maintained thereby at the desired reaction temperature. If desired, the reaction mixture withdrawn from the COOLING ZONE can be passed directly through a heat exchanger to raise the temperature of the reaction mixture up to, or approaching, the desired reaction temperature before said mixture enters the FINAL REACTION ZONE.

The average residence time of reaction mixture in the FINAL REACTION ZONE is determined by the considerations discussed above. In general the average residence time is within the range of about 60 minutes to about 400 minutes depending upon the particular reaction temperature employed. Higher residence times can be employed if desired but offer no practical advantage. Preferably said average residence time is within the range of about 100 minutes to about 240 minutes.

Reaction mixture is withdrawn continuously from said FINAL REACTION ZONE through valve 26 at the same rate as reaction mixture enters said ZONE from the COOLING ZONE via valve 24. A steady state is thereby maintained in the FINAL REACTION ZONE. The reaction mixture withdrawn from said FINAL REACTION ZONE is then passed to a recovery area in which the desired mixture of methylene-bridged polyphenyl polyamines is recovered by procedures routine in the art. Said recovery is carried out either on a batch, or a continuous basis. Said recovery generally comprises neutralization of the reaction mixtue by treatment with excess sodium hydroxide solution followed by separation of the organic phase and stripping of excess aniline therefrom using a conventional evaporator-stripper apparatus. Depending upon the use to which said polyamines are to be put, some or all of the di(aminophenyl)methane can then be recovered by distillation, advantageously using a thin film vacuum distillation apparatus.

In a modification of the process of the invention represented by the partial flow sheet shown in FIG. 3, an additional processing stage is included between the COOLING ZONE stage and the FINAL REACTION ZONE. Said additioinal stage comprises a HOLD ZONE in which the reaction mixture is maintained at a temperature within the range of about 40°C to about 70°C. Reaction mixture is continuously introduced from the COOLING ZONE to the HOLD ZONE and is continuously removed therefrom at the same rate so that a steady state is maintained in the said HOLD ZONE. It has been found that, by maintaining the reaction mixture within said HOLD ZONE within the above temperature range for an average residence time of about 30 minutes to about 240 minutes, it is possible to increase, to a significant extent, the overall yield of di(aminophenyl)methane, as well as the proportion of 4,4'-isomer, obtained in the process of the invention. The residence times in the higher end of the above stated range are employed when the temperature of the HOLD ZONE is maintained in the lower range of temperature stated above, and vice versa.

The said HOLD ZONE can take the form of any of a wide variety of vessels including cylindrical tanks, towers, continuous tubes and the like. In a preferred embodiment the HOLD ZONE comprises a continuous tubular vessel through which the reaction mixture removed from the COOLING ZONE flows in a continuous stream en route to the FINAL REACTION ZONE. Suitable means for supplying heat to, or removing heat from, said tubular vessel can be provided if desired. However, it is generally found that very little exotherm is taking place while the reaction mixture is passing through said HOLD ZONE and it is generally unnecessary to take any steps to control the temperature of the reaction mixture by external means during this stage.

The novel process of the invention has the advantages hereinbefore discussed of (1) enabling the production to take place, on a continuous basis, of methylene-bridged polyphenyl polyamines in which the di(aminophenyl)methane component is present as the substantially pure 4,4'-isomer and (2) of permitting said production of methylene-bridged polyphenyl polyamines to be carried out in very high overall rate of conversion. The ability to operate continuously, as opposed to a batchwise operation, results in considerable savings in labor and a vastly increased total throughput of material for a given plant size. In addition to these advantages the process of the invention provides, for the first time, a means of overcoming a problem which has plagued previous attempts to devise a continuous process for the acid condensation of aniline and formaldehyde. Thus it has been observed hitherto that the bringing together of streams of aniline and formaldehyde in the presence of acid generally gives rise to the deposition from solution of significant amounts of solid material. The exact cause of this deposition, and the chemical composition of the material so deposited, are not fully understood. However, said deposition problem has been of sufficient severity to result in rapid clogging of pipes and constricted areas of reaction vessels and the like. Such clogging rapidly caused shutdown of the processes hitherto devised and prevented said processes being run on a truly continuous basis.

We have now found that, in contrast to the prior art processes, the process of the present invention can be run continuously for prolonged periods of time without any substantial amount of solid deposition taking place in the reaction vessels. This represents a useful and highly unexpected benefit which is additional to all the benefits noted above.

The following examples describe the manner and process of making and using the invention and set forth the best mode contemplated by the inventors of carrying out the invention but are not to be construed as limiting.

EXAMPLE 1

A continuous process for the production of a mixture of polymethylene-bridged polyphenyl polyamines containing approximately 70 percent by weight of di(aminophenyl)methane was carried out as follows.

The apparatus employed was as follows. The mixer nozzle employed to mix the aniline-hydrochloric acid stream and the formaldehyde stream was of the type described in U.S. Pat. No. 3,154,103. The mixer nozzle was mounted, by means of flange and gasket, on to one end of a continuous tubular reactor of 1 inch pipe having a total length of 150 feet. Said reactor was composed of short sections of pipe mounted one above the other in a vertical bank with appropriate elbow sections to provide a continuous coiled tube. The exit port of the tubular reactor was connected, by a suitable control valve and conduit, to a recycle loop containing a centrifugal pump, heat exchanger, and a Kynar lined tank of 500 gallon capacity. The exit conduit from the recycle loop, controlled by an appropriate valve, led via a heat exchanger to a second continuous tubular reactor. The latter was fabricated from 3 inch steel pipe and comprised sections of pipe mounted in a vertical bank and connected by elbows to give a total continuous tube length of approximately 12,000 feet. The reactor was surrounded by a heated bath. The exit from said reactor, controlled by a valve, was connected to a heat exchanger and thence to a neutralization and separation tank for recovery of product.

In carrying out the process of the invention in the above apparatus, the feed aniline-hydrochloric acid stream was an aqueous solution containing 49.1 parts by weight of aniline and 15.7 parts by weight of hydrogen chloride per 100 parts by weight of solution. The formaldehyde feed stream was a 37 percent by weight aqueous solution of formaldehyde. The aniline-hydrochloric acid stream, at a temperature of 35°C to 50°C was fed initially at 10.2 parts by volume per minute to the mixer nozzle. The formaldehyde stream at circa 30°C was fed simultaneously to a mixer nozzle at an initial rate of 2.163 parts by volume per minute. The temperature in the initial tubular reactor was adjusted so that the temperature of the reaction mixture emerging from the exit port and passing to the cooling recycle loop was circa 70°C. The average residence time in the initial tubular reactor was maintained at approximately 32 seconds. The average temperature of reaction mixture in the cooling recycle loop was maintained at 35°C with a rate of flow in said recycle loop of 400 parts by volume per minute. The rate of flow of reaction mixture into said loop, and the corresponding rate of flow of reaction mixture out of said loop, were maintained at 12.36 parts by volume per minute.

The temperature of the reaction mixture entering the FINAL REACTION ZONE was adjusted to 66°C by passage through the heat exchanger. The temperature of reaction mixture in the final tubular reactor was maintaind at about 58°C. The average residence time of the reaction mixture in the second tubular reactor was approximately 400 minutes and the rate of flow of product from said reactor was maintained at 12.36 parts by volume per minute. The product taken from said reactor was cooled to 50°C and then neutralized by addition of excess aqueous sodium hydroxide solution. The organic layer was separated and treated in an evaporator stripper to remove excess aniline. The polyamine product so obtained was subjected to analysis to determine the content of di(aminophenyl)methane, and the 4,4'-isomer content of said di(aminophenyl)methane.

The run was continued for a total of 2½ days. Sixteen hours after the start of operations the rate of formaldehyde feed was increased to 2.22 parts by volume per minute and the temperature of reaction mixture leaving the initial tubular reactor was then observed to be 67°C. Twenty-eight hours after the start of the operation the formaldehyde feed rate was increased to 2.226 parts by volume per minute. The temperature of the reaction mixture, leaving the initial tubular reactor at that time, was observed to be 72°C. Forty-four hours after the start of the operation the feed rate of aniline-hydrochloric acid stream was reduced to 9.12 parts by volume per minute and that of the formaldehyde stream was reduced to 2.016 parts by volume per minute.

The following table shows analytical data obtained on samples of the polyamine product at various stages in the above run.

TABLE I

| Time of Sampling (hr. after start up) | % Diamine | % 4,4'-isomer |
|---|---|---|
| 7.75 | 68 | 98.5 |
| 15.75 | 69.5 | 98.4 |

TABLE I-continued

| Time of Sampling (hr. after start up) | % Diamine | % 4,4'-isomer |
|---|---|---|
| 23.75 | 71.5 | 98.0 |
| 31.75 | 70.0 | 97.8 |
| 39.75 | 68 | 98.5 |
| 47.75 | 70.8 | 98.4 |
| 55.75 | 68.3 | 98.9 |

EXAMPLE 2

A continuous process for the production of a mixture of polymethylene-bridged polyphenyl polyamines containing approximately 37 percent to 48 percent by weight of di(aminophenyl)methane was carried out as follows.

The apparatus employed was that described in EXAMPLE 1 with the exception that (a) the mixer nozzle there used was replaced by a mixer of the type shown in FIG. 2, but having multiple injector tubes 10; (b) the INITIAL REACTION ZONE 6 was changed to 20 feet of ¾ inch diameter pipe and 140 feet of 1-inch pipe in series and (c) a 4,000-foot section of 3-inch pipe was used as a HOLD ZONE between COOLING ZONE and FINAL REACTION ZONE (FIG. 3).

The aniline-hydrochloric acid feed stream was an aqueous solution containing 54.8 parts by weight of aniline and 12.0 parts by weight of hydrogen chloride per 100 parts by weight of solution. The formaldehyde feed stream was 37 percent by weight aqueous formaldehyde solution.

The aniline-hydrochloric acid feed rate was 20.0 parts by volume per minute and the formaldehyde feed rate varied from 5.15 to 5.4 (averaged 5.28) parts by volume per minute. The temperature of the feed stream was circa 35°C to 50°C. The average temperature of the reaction mixture emerging from the initial tubular reactor was 71°C. The average residence time in the initial tubular reactor was 14 seconds, the average temperature of reaction mixture in the cooling recycle loop was 40°C, the rate of flow in the recycle loop was 400 parts by volume per minute, and the rate of flow of reaction mixture into said loop and out of said loop was 25.28 parts by volume per minute.

The temperature of the reaction mixture leaving the HOLD ZONE was 63°C, and the residence time in the HOLD ZONE was about 55 minutes. The temperature was raised to 71°C in a heat exchanger and the temperature of the reaction mixture in the FINAL REACTION ZONE was maintained at 82°C. The average residence time in the FINAL REACTION ZONE was 165 minutes and the rate of flow of product from said reactor was 25.28 parts by volume per minute. The product taken from the final reactor was cooled and worked up as described in EXAMPLE 1. The following Table shows analytical data obtained on samples of the polyamine product at various stages in the above run.

TABLE II

| Time of Sampling After Start of Run (hr.) | % Diamine | % 4,4'-Isomer |
|---|---|---|
| 4 | 44.0 | 98.7 |
| 12 | 41.7 | 99.0 |
| 20 | 37.0 | 99.6 |
| 28 | 40.2 | 98.9 |
| 32 | 48.3 | 99.2 |
| 44 | 44.8 | 98.9 |
| 54 | 44.6 | 99.2 |
| 60 | 46.2 | 99.0 |
| 68 | 47.1 | 99.0 |

TABLE II-continued

| Time of Sampling After Start of Run (hr.) | % Diamine | % 4,4'-Isomer |
|---|---|---|
| 76 | 44.4 | 99.0 |
| 86 | 44.0 | 99.1 |

EXAMPLE 3

As a continuation of the run described in EXAMPLE 2, the aniline, hydrochloric acid, and formaldehyde feed streams were changed without a shutdown to produce a mixture of polymethylene-bridged polyphenol polyamines containing approximately 64 percent to 69 percent by weight of di(aminophenyl)methane.

The aniline-hydrochloric acid feed stream was an aqueous solution containing 48.6 parts by weight of aniline and 15.1 parts by weight of hydrogen chloride per 100 parts by weight of solution. The formaldehyde feed stream was, 37 percent by weight aqueous formaldehyde solution.

The aniline-hydrochloric acid feed rate was initially 20.0 parts by volume per minute and the formaldehyde feed rate was initially 3.84 parts by volume per minute. The temperature of the feed stream was circa 35°C to 50°C. After 20 hours the feed rates were reduced to 15 and 2.81 parts by volume per minute, respectively, and the formaldehyde stream was further reduced to 2.74 parts by volume per minute after 24 hours. At the time the feed rates to the INITIAL REACTION ZONE were reduced (20 hours) a parallel INITIAL REACTION ZONE was activated at ⅔ of these feed rates and fed into the same COOLING ZONE, HOLD ZONE, and FINAL REACTION ZONE. The temperature of the reaction mixture emerging from the initial tubular reactor averaged 62°C, the average temperature of reaction mixture in the cooling recycle loop was 40°C, the rate of flow of the recycle loop was 400 parts by volume per minute. At steady state the parts by weight of flow between reaction sections were equal to the sum of the aniline-hydrochloric acid and formaldehyde feed streams. The temperature of the reaction mixture leaving the HOLD ZONE was circa 60°C. The temperature was raised to 71°C in a heat exchanger and the temperature of reaction mixture in the FINAL REACTION ZONE was maintained at circa 80°C. The product taken from the FINAL REACTION ZONE was cooled and worked up as described in EXAMPLE 1. The following Table shows analytical data, feed rates, and residence times at various stages in the above run.

EXAMPLE 4

A continuous process for the production of a mixture of polymethylene-bridged polyphenyl polyamines containing approximately 64 percent to 72 percent by weight of di(aminophenyl)methane was carred out as follows.

The apparatus employed was that described in EXAMPLE 2.

The aniline-hydrochloric acid feed stream was an aqueous solution containing 47.7 parts by weight of aniline and 15.0 parts by weight of hydrogen chloride per 100 parts by weight of solution. The formaldehyde feed stream was 37 percent by weight aqueous formaldehyde solution.

The aniline-hydrochloric acid feed rate averaged 18.7 (range 14.2 to 19.2) parts by volume per minute and the formaldehyde feed rate averaged 3.58 (range 2.75 to 4.2) parts by volume per minute. The temperature of the feed stream was circa 35°C to 50°C. The average temperature of the reaction mixture emerging from the initial tubular reactor was 56°C. The average residence time in the initial tubular reactor was 18 seconds, the average temperature of reaction mixture in cooling recycle loop was 40°C, the rate of flow in the recycle loop was 400 parts by volume per minute, and the rate of flow of reaction mixture into said loop and out of said loop was 22.28 parts by volume per minute.

The temperature of the reaction mixture in the HOLD ZONE was about 58°C, and the residence time in the HOLD ZONE was about 63 minutes. The temperature was raised to 72°C in a heat exchanger and the temperature of reaction mixture in the FINAL REACTION ZONE was maintained at about 77°C to 79°C. The average residence time in the FINAL REACTION ZONE was 189 minutes and the rate of flow of product from said reactor was 22.28 parts by volume per minute. The product taken from the final reactor was cooled and worked up as described in EXAMPLE 1. The following Table IV shows analytical data obtained on samples of the polyamine product at various stages in the above run.

TABLE IV

| Time (hr.) of Sampling After Start of Run | % Diamine | % 4,4'-Isomer |
|---|---|---|
| 0 | — | — |
| 6 | 64.0 | 98.8 |
| 14 | 72.2 | 98.4 |
| 22 | 70.1 | 98.9 |
| 30 | 65.8 | 99.0 |
| 38 | 70.3 | 98.6 |
| 44 | 71.3 | 98.7 |
| 54 | 71.0 | 98.4 |
| 60 | 69.6 | 98.4 |
| 68 | 71.3 | 98.3 |

TABLE III

| Elapsed Time (hr.) | φNH$_2$-HCl Feed Rate Parts per Min. | Formaldehyde Feed Rate Parts per Min. | Residence Time Initial Reaction Zone Seconds | Residence Time Holding Zone Min. | Residence Time Final Reaction Zone Min. | % Diamine | % 4,4'-isomer |
|---|---|---|---|---|---|---|---|
| 0 | 20 | 3.84 | 17. | 59. | 177 | — | — |
| 12 | 20 | 3.84 | 17. | 59. | 177 | 68.0 | 98.8 |
| 16 | 20 | 3.78 | — | — | — | — | — |
| 20 | 15[1] | 2.81[1] | — | — | — | 64.0 | 98.5 |
| 24 | 15 | 2.74 | 23. | 48. | 144 | — | 99.0 |
| 28 | 15 | 2.74 | 23. | 48. | 144 | 65.3 | 99.0 |
| 36 | 15 | 2.74 | 23. | 48. | 144 | 69.3 | 98.6 |
| 44 | 15 | 2.74 | 23. | 48. | 144 | 67.8 | 98.5 |

[1] Started second INITIAL REACTOR ZONE in parallel with this reactor at same feed ratios and ⅔ of these feed rates. Reactor effluent from both reactors merge in COOLING ZONE.

TABLE IV-continued

| Time (hr.) of Sampling After Start of Run | % Diamine | % 4,4'-Isomer |
|---|---|---|
| 76 | 67.6 | 98.0 |
| 82 | 68.8 | 98.5 |
| 94 | 70.8 | 98.5 |
| 100 | 71.0 | 98.7 |
| 106 | 71.0 | 98.4 |
| 118 | 71.7 | 99.1 |
| 124 | 69.2 | 98.6 |
| 134 | 72.0 | 98.7 |
| 140 | 71.7 | 99.2 |
| 148 | 70.8 | 99.3 |
| 156 | 69.8 | 98.5 |
| 166 | 71.7 | 99.2 |
| 172 | 72.0 | 98.2 |
| 180 | 70.6 | 98.6 |

We claim:

1. A continuous process for the preparation of methylene-bridged polyphenyl polyamines containing di(aminophenyl)methane having a p,p'-isomer content of at least about 98 percent which process comprises the steps of:

intimately intermixing, at a temperature of about 0°C to about 60°C, rapidly flowing fluid streams of aqueous aniline hydrochloride and aqueous formaldehyde, in the proportion of from about 4.0 moles to about 1.5 moles of aniline per mole of formaldehyde, at the entry port of a continuous tubular reactor said aqueous aniline hydrochloride stream having a water content of from 1.3 mole to 7.6 mole per mole of aniline and a hydrogen chloride content of from 0.45 to 0.95 mole per mole of aniline and said aqueous formaldehyde stream having a water content of from 2 moles to 15 moles per mole of formaldehyde;

causing said intermixed fluid streams to flow through said tubular reactor at such a rate that substantially no backmixing occurs while maintaining the temperature of the reaction mixture in said tubular reactor below about 75°C the maximum average residence time in said tubular reactor being about 32 seconds;

continuously passing said reaction mixture from the exit port of said tubular reactor to a cooling zone comprising a continuous loop incorporating a heat exchanger through which said reaction mixture is continuously recycled so as to maintain the temperature of said reaction mixture below about 60°C but above the temperature at which solid material separates from said mixture;

continuously removing reaction mixture from said cooling zone at a rate corresponding to that at which reaction mixture is fed to said cooling zone from said tubular reactor;

continuously passing reaction mixture removed from said cooling zone to one end of a final reaction zone comprising a continuous tube in which the temperature of the reaction mixture is maintained within the range of about 60°C to about 120°C; and continuously removing from the other end of said final tubular reaction zone a mixture of methylene-bridged polyphenyl polyamines at a rate corresponding to that at which the intermediate reaction mixture from the said cooling zone is passed to the final reaction zone.

2. The process of claim 1 wherein the mixing of the aniline hydrochloride and aqueous formaldehyde solutions in the first step of said process is carried out under conditions which give rise to turbulent flow in at least the first portion of said tubular reactor.

3. The process of claim 1 wherein the average residence time in said cooling zone is within the range of about 4 minutes to about 50 minutes.

4. The process of claim 1 wherein the reaction mixture is passed from said cooling zone to said final reaction zone via a holding zone wherein said reaction mixture is maintained at a temperature of about 40°C to about 70°C for an average residence time of about 30 minutes to about 240 minutes.

5. The process of claim 4 wherein said holding zone comprises a continuous tube through which the reaction mixture flows continuously en route to the final reaction zone.

6. The process of claim 1 wherein the mixture of methylene-bridged polyphenyl polyamines removed from said final reaction zone is cooled and neutralized prior to recovery of methylene-bridged polyphenyl polyamines therefrom.

7. A continuous process for the preparation of methylene-bridged polyphenyl polyamines containing about 70 percent by weight of di(aminopheyl)methane having a 4,4'-isomer content of at least 98 percent by weight, which process comprises the steps of:

intimately intermixing at a temperature of about 0°C to about 60°C, rapidly flowing fluid streams of aqueous aniline hydrochloride and aqueous formaldehyde in the proportions of about 2.2 mole of aniline per mole of formaldehyde at the entry port of a continuous tubular reactor said aqueous aniline hydrochloride stream having a water content of from 1.3 mole to 7.6 mole per mole of aniline and a hydrogen chloride content of from 0.45 to 0.95 mole per mole of aniline and said aqueous formaldehyde stream having a water content of from 2 mole to 15 mole per mole of formaldehyde;

causing said intermixed fluid streams to flow through said tubular reactor at such a rate that substantially no backmixing occurs while maintaining the temperature of the reaction mixture in said tubular reactor below about 75°C the maximum average residence time in said tubular reactor being about 32 seconds;

continuously passing said reaction mixture from the exit port of said tubular reactor to a cooling zone comprising a continuous loop incorporating a heat exchanger through which said reaction mixture is continuously recycled so as to maintain the temperature of said reaction mixture below about 60°C but above the temperature at which solid material separates from said mixture;

continuously removing reaction mixture from said cooling zone at a rate corresponding to that at which reaction mixture is fed to said cooling zone from said tubular reactor;

continuously passing reaction mixture removed from said cooling zone to one end of a final reaction zone comprising a continuous tube in which the temperature of the reaction mixture is maintained within the range of about 60°C to about 120°C; and continuously removing from the other end of said tubular final reaction zone a mixture of methylene-bridged polyphenyl polyamines at a rate corresponding to that at which the intermediate reaction mixture from the said cooling zone is passed to the final reaction zone.

8. The process of claim 7 wherein the total water content in the initial reaction mixture entering said tubular reactor is from about 4 to about 7 moles per mole of aniline.

9. The process of claim 7 wherein the reaction mixture is passed from said cooling zone to said final reaction zone via a holding zone wherein said reaction mixture is maintained at about 40°C to about 70°C for an average residence time of about 30 minutes to about 240 minutes.

10. A continuous process for the preparation of methylene-bridged polyphenyl polyamines containing about 50 percent by weight of di(aminophenyl)methane having a 4,4'-isomer content of at least 98 percent by weight which process comprises the steps of:

intimately intermixing at a temperature of about 0°C to about 60°C, rapidly flowing fluid streams of aqueous aniline hydrochloride and aqueous formaldehyde in the proportions of 1.66 mole of aniline per mole of formaldehyde at the entry port of a continuous reactor said aqueous aniline hydrochloride stream having a water content of from 1.3 mole to 7.6 mole per mole of aniline and a hydrogen chloride content of from 0.45 to 0.95 mole per mole of aniline and said aqueous formaldehyde stream having a water content of from 2 mole to 15 mole per mole of formaldehyde;

causing said intermixed fluid streams to flow through said tubular reactor at such a rate that substantially no backmixing occurs while maintaining the temperature of the reaction mixture in said tubular reactor below about 75°C the maximum average residence time in said tubular reactor being about 32 seconds;

continuously passing said reaction mixture from the exit port of said tubular reactor to a cooling zone comprising a continuous loop incorporating a heat exchanger through which said reaction mixture is continuously recycled so as to maintain the temperature of said reaction mixture below about 60°C but above the temperature at which solid material separates from said mixture;

continuously removing reaction mixture from said cooling zone at a rate corresponding to that at which reaction mixture is fed to said cooling zone from said tubular reactor;

continuously passing reaction mixture removed from said cooling zone to one end of a final reaction zone comprising a continuous tube in which the temperature of the reaction mixture is maintained within the range of about 60°C to about 120°C; and continuously removing from the other end of said tubular final reaction zone a mixture of methylene-bridged polyphenyl polyamines at a rate corresponding to that at which the intermediate reaction mixture from the said cooling zone is passed to the final reaction zone.

11. The process of claim 10 wherein the total water content in the initial reaction mixture entering said tubular reactor is from about 4 to about 7 moles per mole of aniline.

12. The process of claim 10 wherein the reaction mixture is passed from said cooling zone to said final reaction zone via a holding zone wherein said reaction mixture is maintained at about 40°C to about 70°C for an average residence time of about 30 minutes to about 240 minutes.

* * * * *